(12) United States Patent
Almoumen (10) Patent No.: US 10,493,204 B2
(45) Date of Patent: Dec. 3, 2019

(54) ASPIRATOR SYRINGE WITH BLOOD DETECTOR

(71) Applicant: Imam Abdulrahman bin Faisal University, Dammam (SA)

(72) Inventor: Saud Abdullah A. Almoumen, Dammam (SA)

(73) Assignee: Imam Abdulrahman bin Faisal University, Dammam (SA)

( * ) Notice: Subject to any disclaimer, the term of this patent is extended or adjusted under 35 U.S.C. 154(b) by 266 days.

(21) Appl. No.: 15/349,060

(22) Filed: Nov. 11, 2016

(65) Prior Publication Data

US 2018/0133400 A1    May 17, 2018

(51) Int. Cl.
*A61M 5/20*    (2006.01)
*A61M 5/31*    (2006.01)

(52) U.S. Cl.
CPC ............ *A61M 5/20* (2013.01); *A61M 5/3137* (2013.01); *A61M 2005/2026* (2013.01); *A61M 2205/583* (2013.01); *A61M 2205/586* (2013.01); *A61M 2205/6081* (2013.01); *A61M 2205/8206* (2013.01)

(58) Field of Classification Search
CPC ............... A61M 5/3134; A61M 2005/2026
See application file for complete search history.

(56) References Cited

U.S. PATENT DOCUMENTS

| 3,448,277 | A | * | 6/1969 | Jayko | ................. | G01N 21/8507 250/573 |
| 3,583,399 | A | | 6/1971 | Ritsky | | |
| 3,732,079 | A | | 5/1973 | Davis | | |
| 5,249,584 | A | * | 10/1993 | Karkar | ............... | G01N 21/0303 356/246 |
| 5,542,934 | A | * | 8/1996 | Silver | ..................... | A61M 5/19 604/191 |
| 5,577,499 | A | * | 11/1996 | Teves | ................. | A61B 5/14542 436/63 |
| 5,690,618 | A | | 11/1997 | Smith et al. | | |
| 5,728,074 | A | | 3/1998 | Castellano et al. | | |

(Continued)

FOREIGN PATENT DOCUMENTS

| GB | 2523591 | B | 3/2016 |
| KR | 2011084247 | A | 7/2011 |
| RO | 126500 | B1 | 4/2012 |

OTHER PUBLICATIONS

"CALAJECT™—computer assisted local analgesia", http://www.ronvig.com/uk/injection/computer-assisted-local-analgesia Screenshot printed date Nov. 10, 2016, pp. 1-7.

(Continued)

*Primary Examiner* — Bhisma Mehta
*Assistant Examiner* — Matthew A Engel
(74) *Attorney, Agent, or Firm* — Oblon, McClelland, Maier & Neustadt, L.L.P.

(57) ABSTRACT

An aspirator syringe comprising a blood-detecting spectrometer. The syringe may accommodate a standard drug cartridge and may provide manual or automatic movement of a plunger for aspiration and injection. Indicator lights may signal the presence or absence of blood in an aspirate within a drug cartridge. The syringe may also include a detector to read a color of a band on a standard drug cartridge in order to identify a drug.

10 Claims, 6 Drawing Sheets

(56) References Cited

U.S. PATENT DOCUMENTS

| | | | | |
|---|---|---|---|---|
| 6,006,583 | A * | 12/1999 | Hayashi | G01N 1/24 600/303 |
| 6,091,490 | A | 7/2000 | Stellman et al. | |
| 7,442,186 | B2 * | 10/2008 | Blomquist | A61M 5/14244 604/152 |
| 7,476,216 | B2 | 1/2009 | Takatsuka et al. | |
| 9,895,494 | B2 * | 2/2018 | Fisher | A61B 17/8836 |
| 2001/0056258 | A1 * | 12/2001 | Evans | A61M 5/31533 604/131 |
| 2004/0064101 | A1 * | 4/2004 | Kowan | A61M 5/14546 604/189 |
| 2004/0162500 | A1 * | 8/2004 | Kline | A61B 5/097 600/532 |
| 2006/0195021 | A1 * | 8/2006 | Esenal | A61B 5/0066 600/310 |
| 2007/0142777 | A1 * | 6/2007 | Klein | G01N 21/11 604/152 |
| 2008/0183122 | A1 * | 7/2008 | Fisher | A61M 5/31511 604/21 |
| 2008/0261261 | A1 * | 10/2008 | Grimes | G01N 33/4905 435/29 |
| 2014/0154399 | A1 * | 6/2014 | Weikart | A61M 5/3129 427/2.3 |
| 2015/0293031 | A1 * | 10/2015 | Fisk | C23C 16/04 356/51 |
| 2016/0228645 | A1 | 8/2016 | Patrick et al. | |
| 2017/0056603 | A1 * | 3/2017 | Cowan | A61M 5/365 |
| 2017/0189621 | A1 * | 7/2017 | Rodiera Olive | A61M 5/31573 |
| 2018/0310954 | A1 * | 11/2018 | Almoumen | A61B 5/0068 |

OTHER PUBLICATIONS

R. Hoad-Robson, "Fine-needle Aspiration" http://patient.info/in/health/fine-needle-aspiration, Nov. 27, 2015, pp. 1-3.

* cited by examiner

ASPIRATOR SYRINGE WITH BLOOD DETECTOR

BACKGROUND OF THE INVENTION

Technical Field

The present invention relates to an aspirator syringe that has a spectrometer to detect the presence or absence of blood within a drug cartridge.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

In performing a nerve block or local anesthetic injection, a medical professional will inject an anesthetic drug into the tissue of a patient at a location where the anesthetic effect is most desired. However, any such injection carries a risk that the syringe needle may puncture or enter a blood vessel. Injecting an anesthetic where it may be circulated by a punctured blood vessel may cause serious adverse reactions to a patient that may necessitate emergency medical care.

Thus, in performing a nerve block or local anesthetic injection, a medical professional uses an anesthetic or aspirating syringe to aspirate a volume of fluid at the injection site. This aspiration is caused by creating a negative pressure in a drug cartridge of a syringe, either by pulling back a piston within the cartridge or by deforming its membrane. The negative pressure causes an aspirated fluid to flow into the drug cartridge, where the medical professional can visually check for the presence of blood while leaving the needle inserted in the tissue. If no blood is present, the drug can be injected in that location, or the medical professional may aspirate again at a different needle depth to further verify the safety of the injection site. If blood is noticed in the cartridge, the medical professional must move the needle and syringe to a different injection site and aspirate again.

In short, the safety of the patient receiving a nerve block or local anesthetic injection depends on the ability of a medical professional to see blood within a drug cartridge, without the benefit of removing the needle from the injection site for a better view. With oral injections, visual blood detection within the drug cartridge can be further difficult due to a lack of contrast, a lack of space, and insufficient lighting within a patient's mouth. There is also a risk that a blood vessel is punctured by the needle but does not produce enough blood that could be noticed by the naked eye.

In view of the forgoing, one objective of the present invention is to provide an aspirator syringe with a built-in spectrometer to detect the presence or absence of blood within an aspirate in a drug cartridge while leaving the needle in place in an injection site.

BRIEF SUMMARY OF THE INVENTION

According to a first aspect, the present disclosure relates to an aspirator syringe that has a hollow syringe barrel with a needle mount extending outwards from a first end of the barrel, a plunger extending from a second end of the barrel and slidably moveable within the barrel, the plunger having a piston-engaging tip extending into the barrel, and a spectrometer attached to an interior side of the barrel, wherein the spectrometer is configured to detect blood in an aspirate.

In one embodiment, the aspirator syringe has a thumb rest attached to an end of the plunger distal to the piston-engaging tip and a finger grip attached to an exterior surface of the hollow syringe barrel adjacent to the second end.

In one embodiment of the aspirator syringe, the piston-engaging tip is a harpoon.

In one embodiment, the aspirator syringe has a battery electrically connected to the spectrometer.

In one embodiment, the needle mount is removably attached to the first end of the hollow syringe barrel.

In one embodiment, the aspirator syringe has a bushing located within the hollow syringe barrel and attached by a spring to the second end. The bushing is traversed by the plunger and configured to secure a drug cartridge within the hollow syringe barrel.

In one embodiment, the spectrometer has an LED light source.

In a further embodiment, where the spectrometer has an LED light source, a fiber optic cable is connected to the LED light source.

In one embodiment, the spectrometer is a spectrophotometer configured to detect an absorbance of a wavelength from 400 to 680 nm.

In one embodiment, the aspirator syringe has a first indicator light on an exterior side of the barrel and electrically connected to the spectrometer to indicate if blood has been detected during aspiration.

In a further embodiment, the aspirator syringe has a second indicator light on an exterior side of the barrel and electrically connected to the spectrometer to indicate if blood has not been detected during aspiration.

In one embodiment, the aspirator syringe has a linear actuator and an electric motor to slide the plunger within the hollow syringe barrel.

In a further embodiment, the linear actuator is at least one selected from the group consisting of a lead screw, a belt drive, a worm drive, a rack and pinion drive, and a chain drive.

In a further embodiment, the aspirator syringe has a button or a switch on an exterior side of the barrel electrically connected to the electric motor.

In a further embodiment, the aspirator syringe having a linear actuator and an electric motor also has a computing device. The computing device may receive a signal from the spectrometer and send an output signal to power the electric motor to actuate the plunger.

In a further embodiment, the aspirator syringe has a second spectrophotometer attached to an interior side of the barrel and electrically connected to the computing device. This second spectrophotometer is configured to detect a color of a cartridge band on an exterior surface of a drug cartridge.

In a further embodiment, the aspirator syringe has a pressure sensor disposed in the plunger and electrically connected to the computing device.

In a further embodiment the aspirator syringe has a piston sensor disposed on the piston-engaging tip and electrically connected to the computing device. This piston sensor is configured to detect engagement between the piston-engaging tip and a piston of a drug cartridge.

In a further embodiment, the computing device also has a digital storage medium to record a position of the plunger within the hollow syringe barrel.

According to a second aspect, the present disclosure relates to a method of administering an anesthetic injection to a tissue of a patient using the aspirator syringe of the first aspect. The method involves inserting an anesthetic syringe needle which is mounted on the needle mount of the aspirator syringe into the tissue of the patient, aspirating an aspirate into a drug cartridge which is loaded into the aspirator syringe and which includes an anesthetic drug, detecting the presence or absence of blood in the aspirate with the spectrometer, and injecting the anesthetic drug into the patient when no blood is detected in the aspirate.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Embodiments of the present disclosure will now be described more fully hereinafter with reference to the accompanying drawings, in which some, but not all embodiments of the disclosure are shown. In the drawings, like reference numerals designate identical or corresponding parts throughout the several views.

According to a first aspect, the present disclosure relates to an aspirator syringe 10 that has a hollow syringe barrel 12 with a needle mount 14 extending outwards from a first end of the barrel 16, a plunger 18 extending from a second end of the barrel 20 and slidably moveable within the barrel, the plunger having a piston-engaging tip 22 extending into the barrel, and a spectrometer 24 attached to a side of the barrel, wherein the spectrometer is configured to detect blood in an aspirate.

Figure 4:
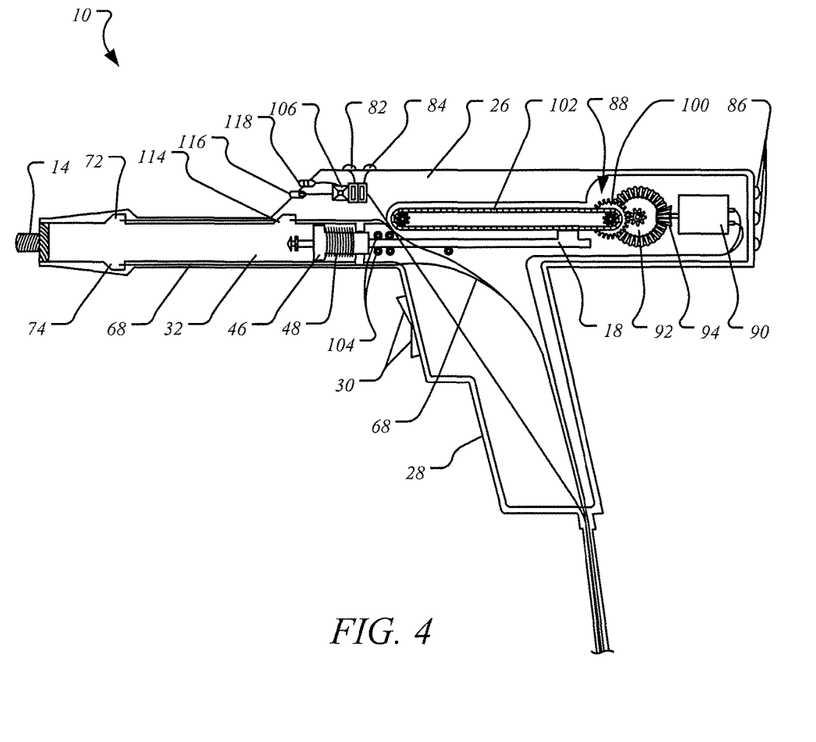
FIG. 4 is a side section view of an aspirator syringe with a plunger connected to a chain drive, and powered by an electric motor.

The hollow syringe barrel 12 may be a cylinder with a diameter of 6-12 mm, preferably 7-11 mm, more preferably 7-10 mm and a length of 50-100 mm, preferably 60-80 mm, more preferably 60-70 mm. The sidewall of the syringe barrel may have a thickness of 0.5-4 mm, preferably 0.7-2 mm, more preferably 0.8-1.2 mm. The sidewall, as well as other parts of the aspirator syringe, may comprise a biocompatible metal, such as stainless steel, aluminum, cobalt, zirconium, titanium, or some other metal. However, non-metals may be used such as polylactic acid (PLA), polylactic-co-glycolic acid) (PLGA), polyvinylchloride (PVC), polyethylene terephthalate (PET), acrylonitrile butadiene styrene (ABS), polypropylene (PP), polystyrene (PS), polytetrafluoroethylene (PTFE), polyetheretherketone (PEEK), polyetherketoneketone (PEKK), polycarbonate (PC), glass, carbon fiber, and/or ceramic. Preferably the barrel is sterilizable by autoclave or other means. In some embodiments, the syringe may comprise an additional casing 26 in order to contain mechanical parts, such as an electric motor and/or gears. In other embodiments, an additional casing may provide a hand grip 28 and electrical switches 30 for the syringe, as shown in FIG. 4. In a related embodiment, a syringe may have a hand grip casing similar to FIG. 4 which is removable, and the syringe may be used with or without the hand grip casing attached.

In a preferred embodiment, the interior of the hollow syringe barrel 32, or the space between the needle mount 14 and the piston-engaging tip 22 of the plunger, is cylindrical and configured to accommodate a standard drug cartridge. The drug cartridge may be used in the injection of local anesthetics for dental and oral procedures. As used herein, the term anesthetic includes any pharmaceutical, medicament, formulation and/or any other fluid, substance or material that causes anesthesia or a loss of sensation. Anesthetics also include drugs that partially destroy nervous tissue. In other embodiments, the syringe may be used for regional anesthesia, peripheral anesthesia, local anesthesia, or nerve block procedures involving injection of one or more anesthetic drugs or other drugs that otherwise influence nerve tissue. Anesthetic drugs include, but are not limited to cocaine, procaine, chloroprocaine, tetracaine, lidocaine, mepivacaine, bupivacaine, etidocaine, prilocaine, and/or levonordefrin. In other embodiments the syringe may be used for injection into a tissue outside of the patient's mouth, for example, in the patient's shoulder, forearm, wrist, thigh, foot, spine, neck, jaw, or an internal organ. In one embodiment, a drug cartridge may contain at least one anesthetic drug and at least one non-anesthetic drug, such as epinephrine. However, in other embodiments, the drug cartridge may include drug or drugs that are not anesthetic, and the syringe may be used in other medical procedures that require an injection, such as a vaccination. In one embodiment, the syringe may be used with non-human animals. In another embodiment, the drug cartridge may be used solely for aspiration, for instance, collecting cells and/or biological fluids for a biopsy, a lab test, or a drug test. Preferably the syringe can accommodate a standard 1.8 mL drug cartridge, and in some embodiments the syringe may be able to accommodate a standard 1 mL drug cartridge, a standard 2.2 mL drug cartridge, and/or other sizes. Preferably the drug cartridge is a transparent glass or plastic cylinder with one end closed by an elastomeric stopper or piston, and with the opposite end comprising an opening sealed with an elastomeric membrane or septum. Preferably the cartridge has a sidewall thickness of 0.8-1.2 mm. In an alternative embodiment, the plunger may comprise a piston that seals against the interior walls of the hollow syringe barrel. In that embodiment, the hollow syringe barrel may be filled directly with a drug solution, without using a drug cartridge or other secondary container.

Figure 1A:
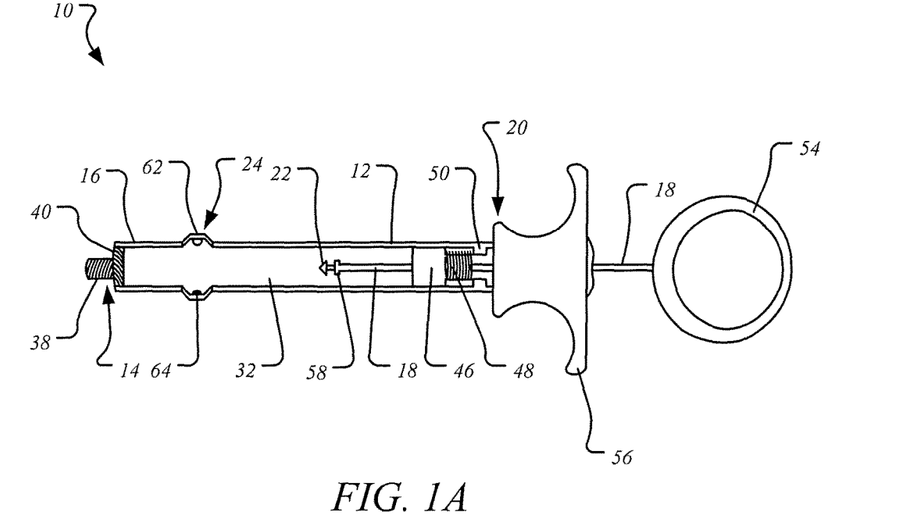
FIG. 1A is a side section view of an aspirator syringe with a spectrometer and manually-driven plunger.
Figure 1B:
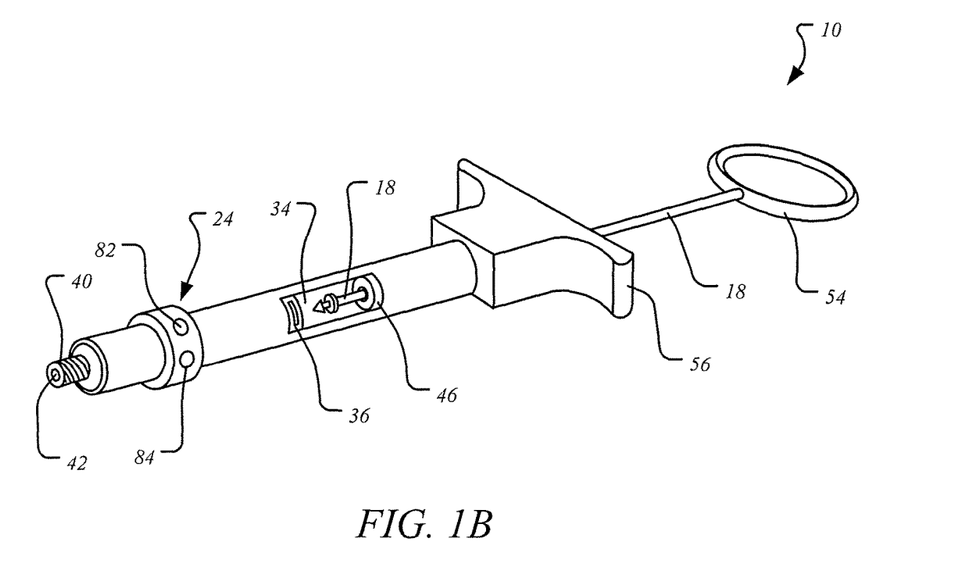
FIG. 1B is a perspective view of the syringe in FIG. 1A.

In one embodiment, the hollow syringe barrel may completely enclose a drug cartridge, so that the cartridge is not visible or exposed to light from outside the syringe. In another embodiment, the exterior of the hollow syringe barrel may comprise one or more openings 34 to expose a portion of the drug cartridge. This may allow a user to visually verify blood in an aspirate, the identity of the drug cartridge, the engagement of the piston-engaging tip in the piston, and/or the position of the piston within the drug cartridge. In one embodiment, one or more openings on the exterior of the hollow syringe barrel may comprise removable or movable covers, such as a sliding cover 36. In another embodiment, an opening on the hollow syringe barrel may be covered with an optical filter so that a user can see inside the drug cartridge without certain ambient light wavelengths interfering with the spectrometer reading. In one embodiment, an opening on the side of the hollow syringe barrel may allow a cartridge to be loaded through the side, and may or may not have a removable or movable cover. FIG. 1B shows an aspirator syringe with opening 34 and sliding cover 36.

In one embodiment, the first end of the barrel has a needle mount 14 extending outwards from the first end of the barrel 16. Preferably the end of the needle mount 38 is threaded to accommodate standard aspirator syringe or dental needles. In an alternative embodiment, other types of needles, tubing, and/or cannulas may be useable with the syringe. In one embodiment, the needle mount is removably attached to the syringe barrel. Here, the needle mount may comprise a second screw thread 40 with the interior of first end of the barrel comprising a complementary thread. To assist in screwing the needle mount on and off, a part of the needle hole 42 may be hexagonal, allowing a hex key to be inserted and used as a screw drive. In an alternative embodiment, the needle hole may comprise a different screw drive or the base of the needle mount may be shaped like a nut, configured to be removed and reattached with a wrench. Alternatively, the needle mount 14 may be removably attached by a different mechanism, such as a clamp, a pin, a bayonet mount, and/or other mechanisms.

In one embodiment, the outer diameter of the removably-attached needle mount at the connection to the first end of the barrel may be equal to the inner diameter of the hollow syringe barrel. In this embodiment, a drug cartridge may be loaded into the hollow syringe barrel when the needle mount 14 is removed, which may be possible with the syringes in FIGS. 1A, 1B, 3, and 4. In another embodiment, the side of the needle mount facing the interior of the hollow syringe barrel may have an annular stud 44, as in FIG. 2. For a manual self-aspirating syringe, this stud may be configured to press against and deform the membrane or septum of a drug cartridge. By then decreasing pressure on the drug cartridge from the plunger end, the membrane becomes less deformed, which creates a negative pressure within the drug cartridge and causes a needle to aspirate into the drug cartridge. The annular stud may have an outer diameter of 1.5-4 mm, preferably 1.5-3 mm, more preferably 1.8-2 mm, an inside diameter of 0.4-3 mm, preferably 0.5-1 mm, more preferably 0.5-0.8 mm, and a height of 0.5-3 mm, preferably 0.6-2 mm, more preferably 0.6-1.8 mm. In an alternative embodiment, the first end of the barrel may have a fixed internal flange, which may or may not have an annular stud. In that alternative embodiment, the diameter of the needle mount at its connection to the barrel may be smaller than the interior diameter of the barrel, and a drug cartridge may be loaded from a side or from the second end of the syringe barrel. Alternatively, the needle mount may be fixed to the syringe barrel, and/or may be machined from the same piece of material.

In one embodiment, the interior of the syringe barrel 32 may be defined by a needle mount or inner flange at the first end and a bushing 46, or hollow cylindrical structure, spaced 50-100 mm, preferably 60-80 mm, more preferably 60-70 mm from the first end of the barrel. This bushing may be attached by a spring 48 to a second inner flange 50 near or at the second end of the syringe barrel. The bushing may be a hollow cylinder with an outer diameter slightly smaller than the inner diameter of the syringe barrel, so that the bushing may slide in the syringe barrel within the range of the spring. The inner diameter of the bushing may be slightly larger than the diameter of the plunger, so that the plunger can slidably and coaxially traverse the bushing and the interior of the syringe barrel. The bushing may also have a segment with a smaller outer diameter, in order to accommodate the spring around its circumference. The entire bushing may be contained in the syringe barrel, as in FIGS. 1A, 1B, 3, and 4, or the end distal the interior may extend outwards, as in FIG. 2. In the embodiment where the bushing is contained, the bushing may have a length of 4-15 mm, preferably 6-12 mm, more preferably 8-12 mm. In the embodiment where the end of the bushing extends out of the syringe barrel, the bushing may have a length of 25-40 mm, preferably 27-37 mm, more preferably 30-35 mm, and may further have an annular flange 52 at the distal end. Preferably the spring is a helical coil spring with a length of 3-13 mm, preferably 4-10 mm, more preferably 6-10 mm, and with an outer diameter of 6-12 mm, preferably 7-11 mm, more preferably 7-10 mm. The winding of the spring may be right or left handed, and the thickness of the wire may be 0.5-1 mm, preferably 0.5-0.9 mm, more preferably 0.5-0.8 mm. The spring may have a pitch of 0.1-4.3 mm, preferably 0.2-3.3 mm, more preferably 0.3-3 mm. Preferably, the spring and the bushing are configured to push a drug cartridge against the inner flange or needle mount in order to secure the drug cartridge within the interior of the syringe barrel, but without deforming the cartridge membrane or blocking the movement of the piston. In one embodiment, the bushing and/or spring are unattached, so that a bushing and/or a spring of a different length and/or compressibility may be exchanged to accommodate drug cartridges of different volumes. In another embodiment, rather than exchanging parts, a single spring and/or single bushing may be able to accommodate drug cartridges of different volumes. In another embodiment, a smaller or larger spring may be used, or more than one spring may be used. In another embodiment, the spring may be located on a different part of the bushing or outside of the bushing yet still provide a compressive force. In another embodiment, instead of a bushing, a washer, a hydraulic piston, a pneumatic piston, an elastomeric material, a compressible element, a sliding brace, some other hollow cylinder, or any combination may be used to secure the drug cartridge. However, in one embodiment, a moveable element may not be needed to hold the drug cartridge, and instead, the cartridge may fit securely between fixed ends of the interior syringe barrel.

As mentioned, the plunger 18 can slidably and coaxially traverse the bushing 46 and the interior of the syringe barrel 32, and in some embodiments, the bushing provides the primary support to coaxially position the plunger within the syringe barrel. In other embodiments, a washer, an annular flange, and/or a second bushing may provide support to the plunger. In another embodiment, the plunger may provide its own support, for instance, the plunger may comprise a segment with a larger diameter that slides within the barrel. In either embodiment, the plunger may slide against the inner surface of the supporting element, or may move on wheels, gears, bearings, and/or lubricant attached to the plunger and/or barrel. In some embodiments, the plunger may be supported and/or attached to a linear actuator mechanism, comprising gears, chains, screws, belts, or some other mechanical part, and in these embodiments the plunger may be rectangular or have a textured surface, such as gear teeth. The plunger may be able to slide and traverse the barrel interior completely from the needle mount 14 to a bushing 46, or the plunger may leave a gap of at least 5 mm, preferably at least 10 mm, more preferably at least 13 mm between the piston-engaging tip 22 and the inner side of the needle mount 14 or inner flange at the first end. The plunger may comprise a total length of 6-150 mm, preferably 7-130 mm, more preferably 90-120 mm. Except for the tip, the plunger may be cylindrical with a diameter of 2-6 mm, preferably 3-5.5 mm, more preferably 4-5.5 mm, or may be some other diameter or shape that allows it to slide freely while being supported within the syringe barrel. Preferably, a length 5-5.5 cm of the plunger adjacent to the piston-engaging tip has a diameter of 6 mm or smaller to allow the plunger to enter a standard drug cartridge as it moves the piston. In some embodiments, the plunger may be completely detached and removed from the hollow syringe barrel. In these embodiments, removing the plunger may allow a drug cartridge to be loaded into the hollow syringe barrel from the second end.

Figure 2:
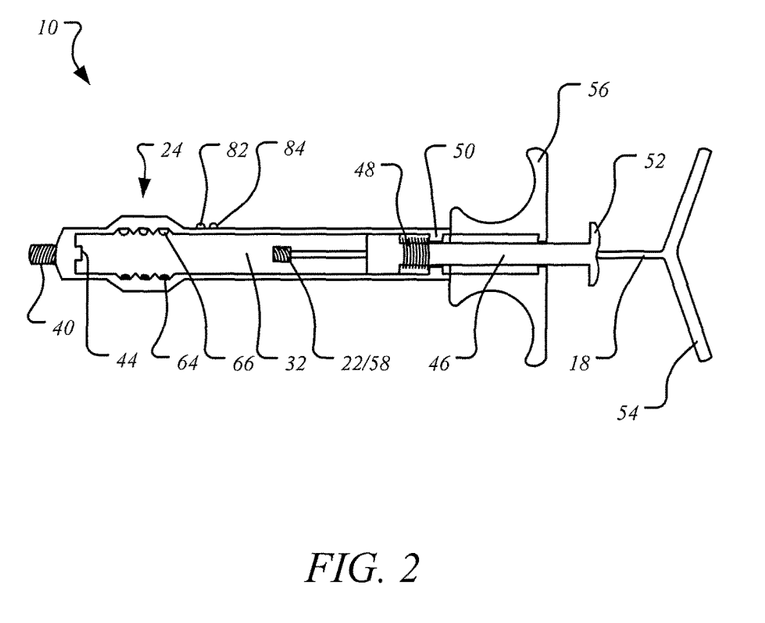
FIG. 2 is a side section view of the aspirator syringe with a spectrometer, manually-driven plunger, and self-aspirating features.

In one embodiment, the end of the plunger distal to the piston-engaging tip is attached to a thumb rest 54. Preferably this part of the plunger extends out and away from the second end of the barrel. In this embodiment, a finger grip 56 is attached to an exterior surface of the barrel adjacent to the second end. The thumb rest may be a ring with a circular or elliptical shape, as in a traditional aspirating syringe, and may have a smallest inner diameter of 15-35 mm, 20-30 mm, more preferably 20-25 mm. FIGS. 1A and 1B show a thumb rest 54 that comprises a ring. Alternatively, the thumb rest may be a bar projecting from the end of the plunger and similar to the thumb rest or palm rest of a manual self-aspirating syringe. FIG. 2 shows a syringe with a bar as a thumb rest 54. The bar may have a length of 20-70 mm, preferably 25-60 mm, more preferably 30-40 mm. In other embodiments, the end of the plunger may have a different shape, such as a disc, to accommodate a user's thumb or other finger, though in some embodiments the plunger may be configured for motorized movement and thus lack a form or a shape for manual control. A finger grip may be in the shape of a T with the stem centered on the central axis of the barrel and plunger. The inner corners of the T may be rounded to better fit a person's fingers. In one embodiment, a syringe with a thumb rest and a T-shaped finger grip may be held in one hand with an index finger and middle finger each in a corner of the T and curved around the cross-bar, with the thumb or palm of the hand on the thumb rest. Preferably the barrel, finger grip, and plunger may all be rotated relative to each other on the same central axis. In one embodiment, the finger grip may comprise two rings or two holes configured for the middle and index finger, or the finger grip may be present in some other form or shape. In the embodiment where the plunger is configured for motorized movement, the barrel may be configured to be held like a pencil, such as the syringe of FIG. 3, and so a textured finger grip may exist on the exterior of the syringe barrel closer to the needle mount. This textured finger grip may be a portion or segments of ribs, ridges, grooves, knurls, bumps, or some other texture. Alternatively, the textured finger grip may be a cushion comprising an elastomeric compound such as silicone rubber, latex, butyl rubber, neoprene, and/or nitrile, and may be solid or comprise air pockets. The cushion may have a height or thickness of 1 mm-4 mm, preferably 1.5-3 mm, more preferably 1.6-2 mm. In other embodiments where the plunger is configured for motorized movement, the external casing of the syringe may be shaped to be held like a power drill, as in FIG. 4. In some embodiments, where the plunger does not have a thumb rest and is configured for motorized movement, the entire plunger may be contained by the syringe barrel and/or an external casing. In other embodiments, a motorized plunger may be housed in a smaller casing where the end of the plunger may protrude from the casing.

In the embodiment where the syringe may be configured for manual self-aspiration, such as the syringe of FIG. 2, the bushing 46 at the second end of the barrel may be connected to an annular flange 52 extending out of the barrel. This annular flange may be disposed between the finger grip 56 and the thumb rest 54, or may be in some other arrangement or shape. The annular flange may have a greatest diameter or width of 8-20 mm, preferably 10-16 mm, more preferably 10-14 mm. Pressing on the annular flange may exert force on a drug cartridge and against an annular stud 44 at the first end of the syringe barrel. This annular stud may deform a drug cartridge membrane, pushing the membrane inwards. Preferably this force on the annular flange or bushing may not influence the position or force on the plunger, as the plunger can freely slide while traversing the bushing. In other embodiments, instead of or in addition to an annular flange, a tab or a button may connect with the bushing and may be located off of the central axis of the syringe barrel and on either side of the finger grip. Sliding this tab or button may create a similar force on the bushing as the force created by pushing on an annular flange.

In one embodiment, the piston-engaging tip 22 of the plunger 18 may be the flat end of a cylinder or rod comprising the plunger. Alternatively, the piston-engaging tip may comprise a second cylinder 58 with a larger diameter and attached concentrically. The second cylinder may have a diameter of 0.2-2 mm, preferably 0.4-1.5 mm, more preferably 0.5-1.2 mm larger than the plunger, and may have a length of 0.5-5 mm, preferably 1-5 mm, more preferably 1-4 mm. In one embodiment, the diameter of the second cylinder does not exceed 6 mm so that it can enter a standard drug cartridge to move the piston. This cylinder may comprise the same material as the plunger or may comprise a different material or an elastomeric material, as listed previously. For a manual syringe configured for self-aspiration, such as the syringe in FIG. 2, the piston-engaging tip 22 may consist solely of the second cylinder 58, or may simply be the end of the plunger. For a plunger with a second cylinder, the second cylinder may prevent the plunger from being completely pulled out and separated from the syringe barrel. Where the syringe has a bushing 46, an inside diameter of the bushing may be smaller than the outer diameter of the second cylinder, to prevent the piston-engaging tip from being pulled completely through. Preferably, however, the second cylinder and the piston-engaging tip can be pulled completely inside a part of the bushing to allow clearance for a drug cartridge to be inserted from a side of the barrel. This may also pull the bushing against a spring 48 to create space for a drug cartridge.

Figure 5:
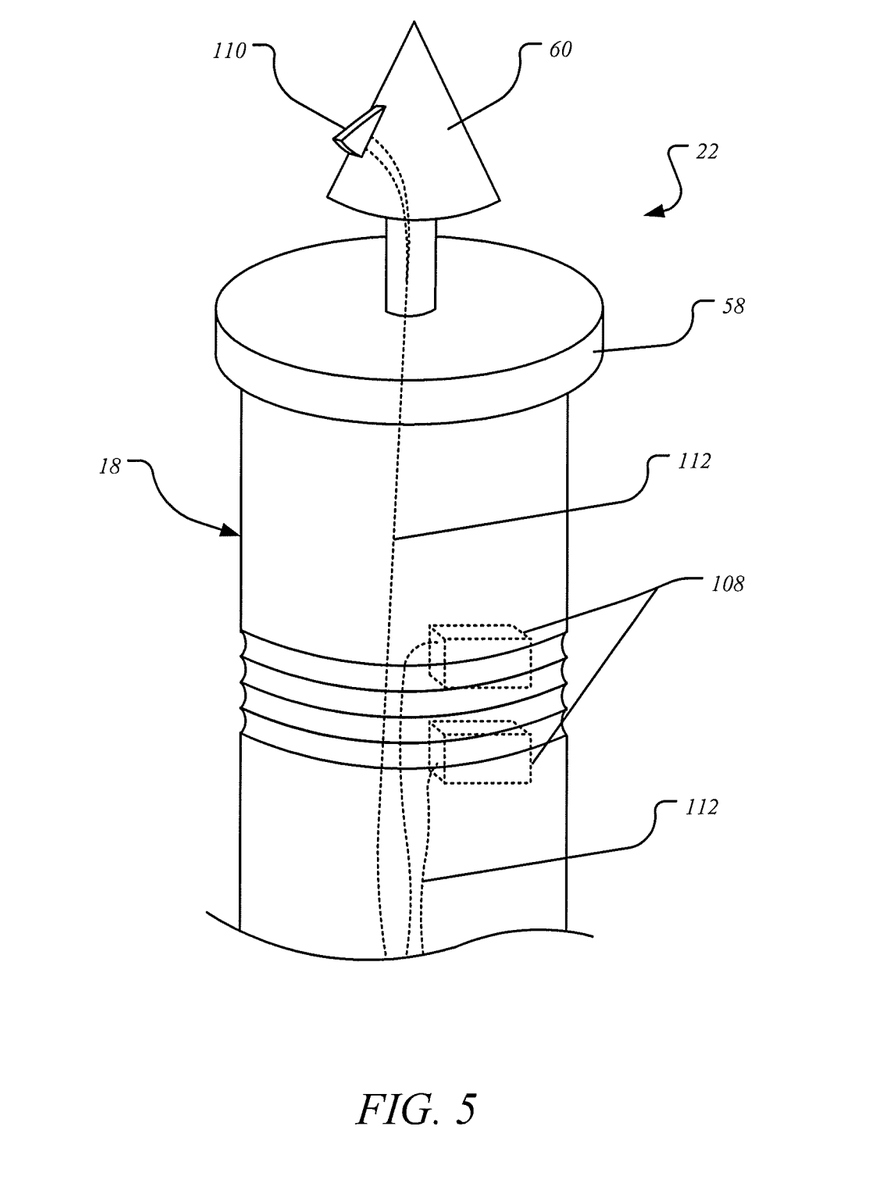
FIG. 5 is a plunger with a pressure sensor and a piston-engaging tip with a piston sensor.

In one embodiment, the piston-engaging tip 22 may comprise a harpoon 60 attached to the end of the second cylinder 58 and extending into the hollow syringe barrel. In the embodiment where there is no second cylinder, the harpoon may instead be attached to the end of the plunger. The harpoon 60 is a shape configured to pierce into and secure within the elastomeric piston of a drug cartridge, so that the plunger 18 is able to move the piston in either direction along the central axis of the syringe barrel. Preferably the harpoon or barb has a pointed tip at an end distal to the plunger. The harpoon may have a pointed shape attached by a shaft to the plunger or second cylinder. The shaft may have a length of 2-6 mm, preferably 2.5-5 mm, and a diameter 0.5-5 mm, preferably 0.5-4 mm, more preferably 0.7-3 mm. The pointed shape may a cone, a pyramid, a spike, a fork, an arrowhead, or may be some other shape. FIG. 5 shows a harpoon 60 with a general cone shape. Preferably the base of the shape is a larger diameter than the shaft in order to resist extraction from a piston, and in some embodiments, the exterior of the pointed shape may comprise one or more barbs to securely engage within the piston. Preferably the piston-engaging tip, including a harpoon if present, does not exceed a diameter or largest width of 6 mm so that it may move within a standard drug cartridge.

In one embodiment, a spectrometer 24 is attached to a side of the barrel and is configured to detect blood in an aspirate. As defined herein, a spectrometer comprises a light source 62 and a photodetector 64 that together may characterize a portion of matter (solid, liquid, and/or gas) based on how the matter changes a property of the light. As defined herein, "light" refers to electromagnetic radiation within the ultraviolet, visible, or infrared wavelength ranges, which together span from 120 nm to 1 mm. The matter may change a property of the light such as intensity, direction, wavelength, and/or polarization. The spectrometer 24 may detect these changes using detection modes such as spectrophotometry, static light scattering, dynamic light scattering, fluorescence, polarization, and/or Raman scattering. The spectrometer comprises one or more photodetectors 64, which may modulate an electric signal in proportion with the intensity of an incident light, with or without specificity towards the wavelength or wavelengths of the light. For example, a single photodetector 64 may generate a similar electric signal when exposed to light of a 280 nm wavelength as for light of a 700 nm wavelength of equal intensity, or it may generate different electric signals. Preferably the spectrometer 24 may detect blood within a portion of the cartridge near the first end of the syringe barrel 16, such as within 8-35 mm, preferably within 10-25 mm, more preferably within 12-22 mm of the membrane of an inserted drug cartridge, or at the end of an aspirating needle within the cartridge.

Preferably the spectrometer 24 may detect whole blood in an aspirate corresponding to a minimum concentration threshold of red blood cells per mL aspirate. The aspirate may be a concentrated stream entering the drug cartridge from an actively aspirating needle, or may be mixed and diluted by a drug solution within the drug cartridge. Preferably the concentration threshold is $10^8$ red blood cells/mL or less, preferably $10^6$ red blood cells/mL or less, more preferably $10^4$ red blood cells/mL or less. In one embodiment, the spectrometer may detect some other component of whole blood, such as plasma, platelets, and/or leukocytes. In one embodiment, the user may be able to raise or set a minimum concentration threshold. In other embodiments, a spectrometer measuring light scattering may be able to determine the velocity, volume, and/or particle size of an aspirate flowing into a drug cartridge. In other embodiments, a spectrometer may detect air bubbles within a drug cartridge.

In one embodiment, where the spectrometer 24 is a spectrophotometer, the spectrophotometer may be able to detect a change in absorbance for an incident light having a wavelength or wavelengths in the range of 200-1050 nm, preferably 300-800 nm, more preferably 400-680 nm. In one embodiment, the spectrophotometer may be tuned to a specific wavelength range corresponding to the absorption of whole blood and/or hemoglobin. This wavelength range may be 342-346 nm, 415-419 nm, 541-549 nm, and/or 573-580 nm. In some cases the wavelength ranges 208-212 nm, 276-280 nm, and/or 342-346 nm may be used for whole blood detection. Where the photodetector detects light scattering, it may measure light that is reflected back in the direction of the light beam, or deflected at an angle or range of angles, for instance, deflected 85-95° relative to the transmission axis of the oncoming beam. In some embodiments, more than one type of photodetector may be present that together share a single light source or more than one light source. In other embodiments, different detectors may work in tandem, for instance, a photodetector for light scattering may be configured with circuitry to monitor for a sudden increase in scattering intensity. This increase in scattering intensity may be a sign of an aspirate, and may then trigger a spectrophotometric detector to take an absorption measurement to determine if the detected aspirate contains blood. In an alternative embodiment, the syringe and spectrometer may be configured to measure a property of an aspirate, with or without injecting a drug. For instance, a blood sample may be taken from a patient and measured within the syringe for hemoglobin concentration and/or oxygen saturation. Other body fluids may be collected and/or measured by the syringe, such as cerebrospinal fluid, bone marrow, and/or joint fluids. In a further embodiment, the syringe may contain a compound for a colorimetric assay to determine other biomolecule concentrations, such as glucose. Other sensors may be used with the syringe, such as a pH sensor. In one embodiment, the needle may comprise a detector to detect the presence or absence of blood or to detect electric conductivity when inserted into a tissue. In one embodiment, a syringe may partially or completely fill a sample cartridge which may then be removed for further testing. In another embodiment, the needle may be used to electrically stimulate a patient's tissue.

In one embodiment, the spectrometer 24 may comprise one or more fiber optic cables 68 connected to one or more light sources 62 and/or one or more photodetectors 64. This may enable a light source, such as a halogen lamp with a diffraction grating, and/or a photodetector, such as a photodiode array, to be housed within a separate casing. However, the one or more fiber optic cables may direct light to or from a photodetector or light source, so that one such fiber optic cable attached to the syringe barrel may be effectively similar to a photodetector or a light source attached to the syringe barrel without a fiber optic cable. Thus, the spectrometer may be considered as being attached to the syringe barrel even if the light source and/or photodetector are connected through fiber optic cables. A light source and/or photodetector, with or without a fiber optic cable, may be connected to a waveguide, as discussed in further detail below.

In an alternative embodiment, the light source may be external, such as light from ceiling lights, a separate instrument, a head lamp, a window, a flashlight, a flame, a lantern, and/or a mounted dental light. In this embodiment, the exterior of the syringe barrel preferably comprises at least one opening 34 to allow the external light to enter the cartridge. In a further embodiment, this opening may be large enough for a user to also see blood aspirated into the cartridge. In one embodiment, the syringe barrel may comprise a sliding cover 36 or covers that may expose one or more areas of the cartridge to external light. In one embodiment, the light source may comprise a gas discharge lamp, an incandescent bulb, a laser, and/or a light emitting diode (LED). In one embodiment, the light source comprises an LED 66, and in a further embodiment, the LED is connected to the spectrometer 24 by a fiber optic cable 68. The connection of the LED to the fiber optic cable may allow illumination near the first end of the syringe barrel, for example, within 8-35 mm, preferably within 10-25 mm, more within preferably 12-22 mm of the membrane of an inserted drug cartridge while using less space than directly attaching the LED near the first end of the syringe barrel. In an alternative embodiment, the light source may be a gas discharge lamp (such as a mercury vapor lamp, a xenon lamp, an argon lamp, or a metal halide lamp), a laser, and/or an incandescent bulb housed in a casing separate from the syringe but attached by a fiber optic cable.

In one embodiment, more than one LED may be used with or without a fiber optic cable to apply light with specific wavelengths. These LEDs may be turned on independently of each other, or more than one may be turned on at a time. The light of different wavelength LEDs may be kept in separate optical fibers, separate fiber optic cables and/or separate waveguides, or combined. Likewise, light from a single light source or multiple light sources may be directed to separate optical fibers or cables based on color. For instance, a single lamp may have a diffraction grating or prism to produce a spectrum of wavelengths, and certain wavelength ranges may be collected by separate fibers to deliver light to a cartridge. Optical shutters may be used to select which wavelengths are delivered.

The fiber optic cable 68 may comprise a single individual fiber or a bundle of more than one fiber, for example, 2-18 fibers. An individual fiber may comprise a core of silica glass, fluoride glass, phosphate glass, chalcogenide glass, and/or plastic, and a cladding of a material with a lower refractive index than the core. In some cases, a photonic-crystal fiber may be used. Examples of cladding include those materials listed for the core, and the core and/or cladding may further comprise a dopant such as $GeO_2$ to modify the refractive index or wavelength transmission. In one embodiment, an optical fiber may be doped with a compound so that the optical fiber additionally acts as an optical filter. A single optical fiber core may have a diameter of up to 50 µm, preferably up to 75 µm, more preferably up to 250 µm, though in one embodiment, a plastic optical fiber may have a core diameter of 250 µm-3 mm comprising poly(methyl methacrylate), polystyrene, and/or some other polymeric material. The optical fiber may have a length of 2-25 cm, preferably 3-20 cm, more preferably 4-18 cm for a light source and/or photodetector located on or in the syringe barrel and/or syringe housing. Alternatively, an optical fiber may have a length of 0.5-3 m, preferably 1-2.5 m, more preferably 1.5-2.5 m for a light source and/or photodetector located in a separate housing. A layer of cladding around the core of a single optical fiber may add to the optical fiber diameter by an additional 20-120 µm. The cladding may furthermore be coated with a layer of polymeric material such as aromatic polyamide or polyvinyl chloride to protect the core from light attenuation caused by physical deformation and/or microbending. A single optical fiber may be a single-mode fiber, a graded-index multimode fiber, or a step-index multimode fiber. Preferably the optical fiber is a step-index multimode fiber.

The fiber optic cable 68 may be mounted along an exterior surface of the syringe barrel, or may be threaded through the syringe barrel 12. In another embodiment, the fiber optic cable 68 may be embedded within a sidewall of the syringe barrel. To avoid being bent, the end of the fiber optic cable may enter into a waveguide 70 as mentioned previously. This waveguide may be a reflective collimator and may comprise a parabolic mirror or reflecting element angled at 42-48°, preferably 44-46° relative to the path of the incident and reflected light, in order to direct the light path so that it enters a cartridge at a substantially perpendicular angle to the cartridge surface. As defined here, "substantially perpendicular" refers to the light passing from the waveguide and through the immediately adjacent cartridge surface at an average angle of 75-105°, preferably 80-100°, more preferably 85-95°, where 90° is a true perpendicular angle. Alternatively, the waveguide may comprise a prism or some other reflecting element, or may comprise a conical or parabolic funnel shape in order to collimate the emitted light. A waveguide directing light to a photodetector may have a similar structure to a waveguide emitting light from a light source. In one embodiment, a fiber optic core may be formed with a bend, angle, and/or curve so that it can direct light substantially perpendicularly into a cartridge without a waveguide. In another embodiment a light source or a photodetector may be used with a waveguide but without an optical fiber.

In one embodiment, the photodetector 64 may be sufficiently small that it can be located within 8-35 mm, preferably within 10-25 mm, more preferably within 12-22 mm of the membrane of an inserted drug cartridge. Alternatively, the photodetector may be located near the end of an aspirating needle inserted in a cartridge where an aspirate may be released into the cartridge. Preferably the size and location of the photodetector does not interfere with the maneuverability of the syringe. The photodetector may comprise one or more Si and/or InGaAs photodiodes, an avalanche photodiode, or a CCD, and may further comprise a filter, a prism, a beam splitter and/or a diffraction grating to select certain wavelengths. In one embodiment, the photodetector may comprise a beam splitter to split the light into RGB channels each with a separate photodiode, similar to a photodetector of a digital camera with color imaging. In another embodiment, the photodetector may comprise a moving filter or diffraction grating, so that a spectrometer collects information on different wavelengths sequentially or produces a spectrum reading. In one embodiment, the photodetector may be connected to a fiber optic cable.

Figure 3:
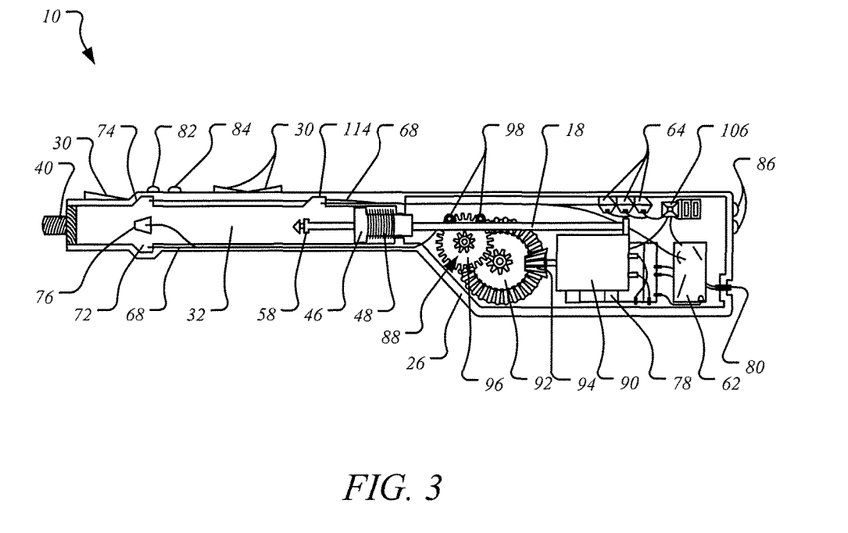
FIG. 3 is a side section view of an aspirator syringe with a plunger driven by a gear and pinion mechanism, which is powered by an electric motor.

In one embodiment, both photodetector 64 and light source 62 of a spectrometer 24 may be connected to separate fiber optic cables 68. In a further embodiment, each fiber optic cable may split into multiple waveguides around the interior of the syringe barrel. This split may be possible with a prism or by using individual fibers that are bundled as one cable at the photodetector and/or light source. Multiple waveguides may be arranged on a circumference around the cartridge, preferably with one side limited to photodetector waveguides 72 and the other side limited to light source waveguides 74. Preferably, the number of photodetector waveguides is equal to or greater than the number of light source waveguides. In one embodiment, the photodetectors and light sources may be located circumferentially around the syringe barrel at the same length along the syringe barrel. In another embodiment, the photodetectors and light sources may be located at different lengths along the syringe barrel. The photodetectors and/or light sources may or may not be connected to waveguides and/or fiber optic cables. In a related embodiment, light may be directed from a light source at one length along the syringe barrel, and this light may be collected by a photodetector at a different length along the syringe barrel. For instance, a light source may be positioned in the hollow syringe barrel near the neck of a drug cartridge, which may be 2-7 mm, preferably 3-6 mm from the interior of the needle mount. This light source may direct a beam of light through a central axis of a cartridge and into a photodetector located in the hollow syringe barrel 12-20 mm, preferably 14-16 mm from the interior of the needle mount. The light from one or more light sources may be directed through a central axis of the cartridge, or the light may be directed as parallel rays across the interior of the cartridge. Preferably the light crosses within a 3 mm radius, preferably within a 2 mm radius, preferably within a 1 mm radius of the central axis of the syringe barrel, in order to more likely intersect with an aspirate formed in a drug cartridge. A light source or light source waveguide may emit light rays within a narrow or broad range of angles. For instance, light rays emitted with narrow angles may comprise rays where the maximum angle between any two rays is 6° or less, preferably 5° or less, more preferably 4° or less. In contrast, a light source or light source waveguide may emit light rays at wider angles. For instance, the light emitted may comprise light rays spread over an angle of at least 40°, preferably at least 50°, more preferably at least 70°. Where light is emitted at an angle, it may be emitted from a slit, or may form a conical shape or some other form. The light may have a long or short coherence length, may be emitted in pulses or in a steady state, and may or may not be polarized. Where a light source or light source waveguide emits parallel rays of light, preferably the maximum distance between any two parallel rays may be less than 6 mm, preferably less than 5 mm, more preferably less than 4 mm. Where light is emitted in parallel rays, it may be emitted as a flattened beam of light, such as light from a rectangular slit, or may have a circular or elliptical cross-section, or some other shape. In related embodiments, similar to what has been described for emitted light, photodetectors and photodetector waveguides may be configured to collect parallel rays of light, light rays spread over certain angles, light arriving from certain locations of a drug cartridge, and/or certain shapes of light beams. The light source, photodetector, and/or waveguides may comprise one or more polarizers, lenses, slits, diaphragms, apertures, prisms, lenses, screens, filters, diffraction gratings, shutters, reflectors, phosphorescent material, and/or other optical structures to manipulate light. In one embodiment, more than one light source waveguide in a syringe barrel may emit light at separate times. In one embodiment, where the light source waveguides connect with separate light sources, the waveguides may each direct light of different wavelengths. In one embodiment, all light sources are turned on and measured at once by all photodetectors. In another embodiment, one light source is turned on while all the detectors collect and quantify the light. In this way, the detector positioned directly across from the light source can measure the absorption at a wavelength, and the other detector or detectors can measure an amount of light scattering. An example of this embodiment is shown in FIG. 3, where the light source waveguide 74 is positioned in the hollow syringe barrel 12 directly across from a first photodetector waveguide 72. A second photodetector waveguide 76 is positioned in the hollow syringe barrel and configured to collect a portion of light scattered substantially perpendicularly from the light path between the light source waveguide 74 and the first photodetector waveguide 72. The photodetector linked to the first photodetector waveguide may be used to measure an absorption spectrum. The photodetector linked to the second photodetector waveguide may measure an intensity of light scattering or may be used to measure fluorescence or Raman scattering. In one embodiment, the light source, photodetector, and other electronics may be removably attached to the syringe barrel or syringe housing. In this embodiment, the light source, photodetector, and other electronics may be replaced or sterilized by a sterilization method safe for electronics, and the rest of the syringe may be sterilized separately, for example, by autoclaving.

In one embodiment, where the light source 62 and the photodetector 64 are each connected to at least one optical fiber, those optical fibers may be bundled together in a single cable as a reflectance probe which terminates at a single waveguide. Here, at least one optical fiber of the bundle may emit light while at least one optical fiber may collect light that is scattered or emitted back along the path of transmission, which may also include fluorescence emission. In one embodiment, the reflectance probe comprises at least six optical fibers connected to a light source, and at least one optical fiber connected to the photodetector. The fibers of the reflectance probe may terminate with the photodetector optical fiber surrounded by the light source optical fibers. In one embodiment, a reflectance probe may be positioned across from a second photodetector or a waveguide linked to a photodetector that may measure transmitted light.

In an alternative embodiment an aspirate may be measured within a flow cell, rather than inside the drug cartridge. In this embodiment, instead of a traditional dental needle or aspirating syringe needle, the aspirate arriving from a needle feeds into a flow cell before entering the drug cartridge, and the flow cell may have a similar thickness as the needle diameter. Here, the photodetector and/or light source, with or without a connection to a fiber optic cable, may be located at the flow cell. This may enable a spectrometer to detect blood with a higher sensitivity as the aspirate may be less diluted than an aspirate in a drug cartridge. Alternatively, the syringe may comprise separate fluid paths for aspiration and injection. For example, an aspirating step may direct an aspirate into a flow cell or other sampling chamber without allowing the aspirate to enter into a drug cartridge. Then, an injection step may direct the flow of a drug through the same needle, with or without bypassing a flow cell or sampling chamber. In another alternative embodiment, a flow cell may measure other properties of an aspirate, such as electrical conductivity or temperature.

In one embodiment, the aspirator syringe has a battery 78 electrically connected to the spectrometer 24. The battery may comprise one or more alkaline, lithium, lithium-ion, nickel-cadmium, nickel metal hydride, zinc-air, silver oxide, and/or carbon-zinc electrochemical cells. The electrochemical cells may be wired in parallel, in series, or a combination of both. Preferably the battery is rechargeable. The battery may have a nominal capacity of 10-1500 mAh, preferably 20-1100 mAh, more preferably 30-700 mAh. In an alternative embodiment, the aspirator syringe does not have a battery and is powered by an AC adaptor or other power source. In one embodiment, this battery may provide power to other electronic components of the syringe, such as lights, motors, cameras, sensors, and/or computer circuitry. Preferably the exterior of the syringe has a socket, plug, electric contacts, and/or some other electrical connection to recharge a rechargeable battery, or the battery may be charged inductively without an exterior connection. FIG. 3 shows a syringe with both a battery 78 and an electric connection 80 for recharging the battery. Alternatively, the exterior of the syringe may have a door or removably attached cover to access and exchange batteries.

In one embodiment, the aspirator syringe has a first indicator light 82 on an exterior side of the barrel and electrically connected to the photodetector 64 to indicate if blood has been detected during aspiration. In a further embodiment, there may be a second indicator light 84 on an exterior side of the barrel, also electrically connected to the photodetector 64, and which indicates if blood has not been detected during aspiration. Preferably these lights are located on the side of the barrel near the first end of the barrel 16, within the first 50%, preferably the first 40%, more preferably the first 30% of the length of the barrel adjacent to the first end. Preferably one or both of the lights are LEDs, though other types of electric lights may be used. Preferably the lights are located where they may not be obscured by the hand of a person delivering the injection. In one embodiment, the lights may be located near the second end of the barrel, or elsewhere on the syringe housing, for example, at the end of the syringe housing opposite to the needle mount. In one embodiment, a single, multi-colored light may be used to indicate either the presence or absence of blood. In another embodiment, one or more indicator lights may be scaled by intensity or form a number in order to indicate the certainty of detecting blood, or the strength of an absorption measurement and/or a light scattering measurement, and/or the battery capacity. In one embodiment, a third indicator light may be used to indicate that an aspirate has been detected, but blood has not been detected. Alternatively, a third indicator light could indicate if the absorbance or light scattering values are too low, too high, or out of a specific range. This may indicate that a light source and/or photodetector are malfunctioning and/or unintentionally blocked. In another embodiment, additional indicator lights 86 may be placed on the exterior of the syringe barrel and/or syringe housing, and may be in different locations than the first and second indicator lights. In an alternative embodiment, the aspirator syringe may have speakers 622 to generate certain sounds or melodies in order to convey similar information from the spectrometer relating to blood in the aspirate.

In one embodiment, the aspirator syringe has a linear actuator 88 and an electric motor 90 to slide the plunger 18 within the hollow syringe barrel 12. In this embodiment, the entire plunger may be contained within the hollow syringe barrel and/or a syringe casing 26, or the end distal the piston-engaging tip may protrude from the syringe barrel and/or casing. The linear actuator is a mechanism or set of mechanisms that convert the rotational motion of the motor into translational motion on the plunger. Preferably the electric motor runs on DC power. The electric motor may be a brushed or brushless DC motor, a switched reluctance motor, a universal motor, a stepper motor, a servomotor, an axial rotor motor, or some other type of motor. In an alternative embodiment, the motor may be an AC asynchronous motor, such as a shaded pole motor, or an AC synchronous motor, such as a hysteresis motor, or some other AC motor. Preferably, a gear train may exist to reduce the rotational motion coming directly from the electric motor. The gear train may have a double gear with a bevel edge 92 that connects with a bevel gear 94 on the motor shaft. The connection of these two gears allows the motor to be placed with its rotational axis parallel with the longitudinal axis of the syringe barrel, so that the motor does not significantly protrude. The double gear with the bevel edge 92 may drive one or more double gears 96, one of which may connect to a linear actuator 88. The linear actuator may be a lead screw, a belt drive, a worm drive, a rack and pinion drive, a chain drive, or some combination thereof. In some embodiments, the plunger 18 may be directly involved as a mechanical part, for instance, a surface of the plunger parallel with its central axis may comprise gear teeth in order to form a rack for a rack and pinion drive. This type of linear actuator is shown in FIG. 3. Here, the teeth of the inner gear of the double gear 96 mesh with the teeth on the surface of the plunger 18. Additional gears 98 are attached to the housing and hold the plunger against the double gear 96 as the plunger moves. In this embodiment, the plunger shaft has gear teeth on opposite sides, though in other embodiments the plunger may only have gear teeth on one side, and/or a bushing may support the position of the plunger.

In other embodiments, a side of the plunger may be attached to a linear actuator. For example, the end of the plunger distal the piston-engaging tip may be attached to a chain in a chain drive mechanism or to a lead screw in a traveling screw mechanism. In FIG. 4, a plunger 18 is connected to a chain drive. Here, a double gear 100 comprises a chain sprocket to drive a chain 102 within the syringe. A side of the plunger 18 is attached to the chain 102 and the plunger is held in position by guide wheels 104. In one embodiment where the plunger is moved by a motor or other mechanical means, a bushing may be sufficient to support the position of the plunger. Preferably an electric motor and linear actuator are able to move a plunger to engage the piston-engaging tip with a piston of a drug cartridge, and move the piston towards the membrane-capped end of the drug cartridge until coming into contact with the membrane or neck of the drug cartridge, or a needle inserted into the drug cartridge. Preferably an electric motor and linear actuator are able to move a piston in the opposite direction away from the membrane-capped end of a drug cartridge.

Alternatively, other actuators may be used, with or without rotational motion from a motor. For instance, the end of the plunger distal to the piston-engaging tip may comprise a hydraulic or pneumatic piston, so that the translational motion of the piston is controlled by air or fluid pressure. Alternatively, the plunger may be driven by a linear electric motor, or by the energy contained in a wound-up or compressed spring. In one embodiment, a plunger may be attached and movable by a linear actuator and electric motor, but also have a thumb rest to allow for manual movement of the plunger. In some embodiments, a sensor, a structure, and/or a device in the motor, syringe barrel, and/or linear actuator may prevent the motor from pushing the plunger beyond certain lengths in the syringe. In a further embodiment, a feedback mechanism or circuitry exists in the syringe barrel or in the motor that can tell the position of the plunger. In another related embodiment, optical, magnetic, electric, acoustic, or mechanical sensors may exist along the interior of the syringe barrel in order to detect the position of the plunger and/or the piston. In one alternative embodiment, a drug cartridge and plunger may be located in a separate module connected to a handle by flexible tubing that carries the drug. Here, the handle may comprise a needle and a spectrometer.

In a further embodiment, the aspirator syringe may have a button or a switch 30 on an exterior side of the barrel electrically connected to the electric motor 90. The button or switch on the side of the syringe may control the position of the plunger towards or away from the first end, and there may be more than one button or more than one switch. In other embodiments, a button or switch may turn the syringe on or off, or start an automatic aspiration and/or injection routine. Preferably the button or switch is positioned on the syringe where a user can access the button without changing his or her grip on the syringe. In an alternative embodiment, a foot pedal electrically attached to the motor may provide the same control, or a foot pedal may control the motor through a wireless transmitter. The button, switch, and/or foot pedal control may move the plunger at a single speed in each direction or at variable speeds. In one embodiment, an indicator light may comprise a button or a switch.

In a further embodiment, the aspirator syringe having a linear actuator and an electric motor also has a computing device 106. The computing device may receive a signal from the spectrometer 24 and send an output signal to power the electric motor 90 to actuate the plunger 18. In this embodiment, preferably a feedback mechanism, as mentioned previously, exists for the computing device to detect the position of the plunger. The feedback mechanism may involve a calibration step, such as moving the plunger between two limits of a range of positions within the hollow syringe barrel, before a user loads a drug cartridge. In some embodiments, the computing device may send a signal to turn on and/or control the spectrometer.

Next, a hardware description of the computing device 106 according to exemplary embodiments is described with reference to FIG. 6. Here, the computing device 106 includes a CPU 600 which performs the processes described above/below. The process data and instructions may be stored in memory 602. These processes and instructions may also be stored on a digital storage medium 604 such as a hard drive (HDD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk, solid-state drive, and/or any other information processing device with which the computing device communicates, such as a server or computer. In one embodiment, the digital storage medium 604 comprises a memory card that can be removed and exchanged. The digital storage medium of the computing device may have a formatted capacity of 1 MB-10 GB, preferably 10 MB-5 GB, more preferably 100 MB-4 GB.

Further, the claimed advancements may be provided as a utility application, background daemon, or component of an operating system, or combination thereof, executing in conjunction with CPU 600 and an operating system such as Microsoft Windows 7, UNIX, Solaris, LINUX, Apple macOS, and other systems known to those skilled in the art.

The hardware elements of the computing device may be realized by various circuitry elements, known to those skilled in the art. For example, CPU 600 may be a Xenon or Core processor from Intel of America or an Opteron processor from AMD of America, or may be other processor types that would be recognized by one of ordinary skill in the art. Alternatively, the CPU 600 may be implemented on an FPGA, ASIC, PLD, or the CPU may use discrete logic circuits, as one of ordinary skill in the art would recognize. Further, the CPU 600 may be implemented as multiple processors cooperatively working in parallel to perform the instructions of the inventive processes described above and below.

Figure 6:
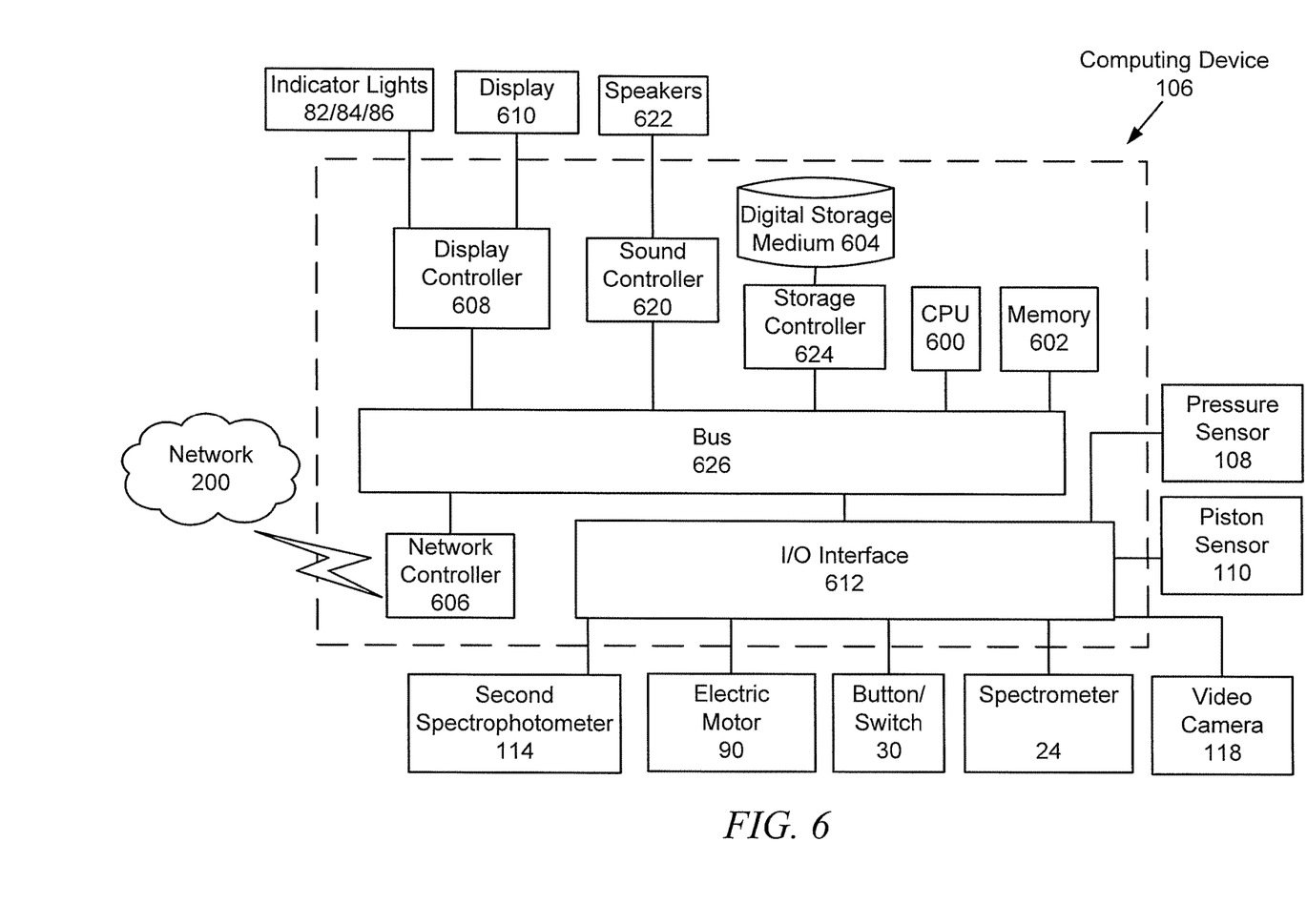
FIG. 6 is a diagram of a computing device connected to components of an aspirator syringe.

The computing device in FIG. 6 may also include a network controller 606, such as an Intel Ethernet PRO network interface card from Intel of America, for interfacing with a network 200. As can be appreciated, the network 200 may be a public network, such as the Internet, or a private network such as an LAN or WAN network, or any combination thereof, and may also include PSTN or ISDN subnetworks. The network 200 can also be wired, such as an Ethernet network, or can be wireless such as a cellular network including EDGE, 3G, and 4G wireless cellular systems. The wireless network can also be WiFi, Bluetooth, ANT, DASH7, ISA100.11a, MiWi, near-field communication, OCARI, ONE-NET, TSMP, WirelessHART, ZigBee, Z-Wave, and/or any other known form of wireless communication.

The computing device 106 may include a display controller 608, such as a NVIDIA GeForce GTX or Quadro graphics adaptor from NVIDIA Corporation of America. The display controller 608 may interface with a display 610, such as an LED or LCD display located on an exterior surface of the syringe. The display controller 608 may also interface with indicator lights 82/84/86 on the syringe. A general purpose I/O interface 612 may interface with switches or buttons 30 on the syringe, with the spectrometer 24, with a second spectrophotometer 114, with a piston sensor 110 in the piston-engaging tip, with a pressure sensor 108 in the plunger, and/or with a video camera 118.

A sound controller 620 may be provided in the computing device 106, such as Sound Blaster X-Fi Titanium from Creative, to interface with speakers 622 to provide alerting sounds or melodies.

A general purpose storage controller 624 may connect to a digital storage medium 604 with communication bus 626, which may be an ISA, EISA, VESA, PCI, or similar, for interconnecting all of the components of the computing device 106.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset.

As mentioned, the computing device 106 may be electrically connected to a pressure sensor 108 in the plunger 18 and/or a sensor 110 in the piston-engaging tip 22. For example, in one embodiment the piston-engaging tip may have a sensor configured to detect if the piston-engaging tip 22 is engaged within a piston of a drug cartridge. This sensor may be a mechanical switch on an exterior surface of a harpoon 60. When the harpoon is not engaged in a piston, the switch may protrude from the harpoon surface, and while engaged within a piston, the switch may lie against the surface of the harpoon, or in a different position. These two configurations of the switch may correspond to opening or closing a circuit, which may send a signal to the computing device. In an alternative embodiment, the switch on the harpoon may provide a catch that holds the harpoon within the piston, and following an injection, the switch may have a mechanism to withdraw itself into the harpoon so that the harpoon can more easily be removed from the piston. Alternatively, the sensor may be a piezoelectric element which creates a change in electric charge when under pressure, or the sensor may be piezoresistive, electromagnetic, and/or inductive, or the sensor may be able to modify some other property of electricity, magnetism, and/or electromagnetic radiation. In an alternative embodiment, the harpoon may comprise a pressure sensor relying on hydraulics, pneumatics, and/or optics. In one embodiment, the harpoon may comprise more than one type of sensor, or the plunger or second cylinder may comprise a sensor that can similarly tell if the piston is engaged. Preferably the sensor is electrically connected by wiring 112 threaded through the plunger to the computing device.

As mentioned, in one embodiment, the plunger 18 has a pressure sensor 108. Preferably this pressure sensor may be configured to measure the pressure being applied from the plunger to a piston, after the piston-engaging tip is engaged in the piston. This pressure sensor may be piezoelectric, piezoresistive, or a sensor of another type as listed previously. The pressure sensor may be located anywhere along the length of the plunger, but preferably the sensor is located on a portion of the plunger closer to the piston-engaging tip, for example, within 5-15 mm, preferably within 7-13 mm, more preferably within 7-12 mm of the piston-engaging tip. Preferably the pressure sensor is electrically connected to the computing device 106 by wiring 112 threaded through the plunger. Preferably the pressure sensor may detect a positive or negative pressure of an absolute value of at least 500 Pa, preferably at least 100 Pa, more preferably at least 10 Pa. In one embodiment, the pressure sensor may detect a certain absolute pressure on the plunger, for example, 60-200 kPa, and send a signal to the computing device and/or an indicator light to indicate malfunction. In one embodiment, a user may adjust certain pressure thresholds in order to stay within a certain pressure range, or trigger an alert at different pressures. FIG. 5 shows an example of a plunger 18 with a pressure sensor 108. The plunger also has a mechanical switch 110 projecting from the exterior surface of a harpoon 60 which can detect when the harpoon is engaged inside a drug cartridge piston.

In one embodiment the computing device may record a position of the plunger within the syringe barrel. Where the computing device senses and records two positions of the plunger, it may calculate a corresponding change in the cartridge volume. The computing device may record other information delivered to it by other sensors. This information may relate to changes in injection pressure, values of spectrometer readings, time and date, and/or the identity of the drug injected.

In a further embodiment, the aspirator syringe has a second spectrophotometer 114 attached to an interior side of the barrel and electrically connected to the computing device 106. This second spectrophotometer is configured to detect a color of a cartridge band on an exterior surface of a drug cartridge. Preferably the cartridge band is 2.5-3.5 mm, preferably 2.8-3.2 mm wide and located 10-20 mm, preferably 13-16 mm from the piston end of the cartridge. Thus, the second spectrophotometric sensor may be located on an interior side of the syringe barrel, 10-20 mm from where a bushing may hold the piston end of the cartridge. For a standard 1.8 mL drug cartridge, the sensor may be located 48-54 mm from the inner flange or inner side of the needle mount at the first end. As the cartridge band may be opaque, the spectrophotometer light source may be configured to emit light at an angle with an adjacent detector configured to collect the reflected or scattered light. As mentioned previously with the blood-detecting spectrometer, the light source and/or photodetector may be connected by fiber optic cables and/or waveguides to the side of the barrel. In one embodiment, both light source and photodetector are connected by one or more optical fibers and are bundled into a single cable as a reflectance probe, as mentioned previously. FIG. 3 and FIG. 4 show syringes where the second spectrophotometric detector 114 comprises a single waveguide with a reflectance probe, which is located in a position to coincide with the cartridge band of a drug cartridge.

Preferably the cartridge band is color coded according to the drug contents, in spite of different drug manufacturers. For lidocaine 2% with epinephrine 1:100,000, preferably the cartridge band color is red, such as Pantone Matching System (PMS) colors 185 C, 186 C, 199 C, and/or 200 C. For lidocaine 2% with epinephrine 1:50,000, preferably the band is green, such as PMS 347 C, 348 C, 355 C, and/or 356 C. For mepivacaine 2% with levonordefrin 1:20,000, preferably the band is brown, such as PMS 471 C, 477 C, 478 C, 498 C, and/or 499 C. For mepivacaine 3%, preferably the band is tan, such as PMS 466 C, 467 C, and/or 468 C. For prilocaine 4% with epinephrine 1:200,000, preferably the band is yellow, such as PMS 108 C, 109 C, 110 C, 115 C, and/or 116 C. For prilocaine 4%, preferably the band is plain black, such as PMS P 179-16 C. For bupivacaine 0.5% with epinephrine 1:200,000, preferably the band is blue, such as PMS 300 C and/or 301 C. For articaine 4% with epinephrine 1:100,000, preferably the band is gold, such as PMS 871 C, 872 C, 873 C, 874 C, and/or 875 C. For articaine 4% with epinephrine 1:200,000, preferably the band is silver, such as PMS 877 C. Other colors may be reserved for other drugs, concentrations, and/or mixtures of drugs. In another embodiment, radiofrequency tags, barcodes, magnetic encoding, or computer-readable text may be used instead of band color. In one embodiment, the computing device 106 may correlate a cartridge band color with a drug concentration, and store the concentration value in its digital storage medium 604. Based on this concentration, the computing device in the syringe may calculate the mass of a drug injected based on the position of the plunger. In a related embodiment, a user may set a volume or mass of a drug to be delivered, and the computing device may move the plunger to inject that amount of drug. In an alternative embodiment, a user may override or change a color coding stored in the computing device. For example, a user may set a yellow cartridge band color to correspond to a different drug and/or concentration than that listed above.

In one embodiment, the exterior of the syringe may comprise an LCD or LED display 610 linked to the computing device 106. This screen may convey information relating to the identity of the drug, the injection flowrate, the injection pressure, the injection volume, the presence of an aspirate, the presence of blood in an aspirate, the patient's identity, the battery capacity, values of biomarkers such as hemoglobin concentration, wireless connectivity, and/or other parameters. In another embodiment, the syringe may comprise a wireless transceiver or a network controller 606 as previously described in order to wirelessly transmit such information to a computer or a separate electronic device. In another embodiment, a cable comprising one or more fiber optic cables and/or electric wiring to a power source may also comprise a data cable for the syringe to exchange the same type of information. In another embodiment, the exterior of the syringe may comprise one or more lights for illumination within a patient's mouth and/or a video camera to help a user guide the needle. FIG. 4 shows an aspirator syringe 10 with an illumination light 116 and a video camera 118. In the embodiment where the syringe comprises a video camera, a screen or display 610 may be attached to the syringe to display a real-time image. Alternatively, the video images may be delivered to an external computer monitor or a separate instrument module. In another embodiment, a digital storage medium 604 within the syringe may store a video.

According to a second aspect, the present disclosure relates to a method of administering an anesthetic injection to a tissue of a patient with the aspirator syringe of the first aspect. The method may involve loading a drug cartridge containing an anesthetic drug into the aspirator syringe 10, attaching an anesthetic syringe needle to the needle mount 14, inserting the anesthetic syringe needle into the tissue, aspirating an aspirate into the drug cartridge, detecting the presence or absence of blood in the aspirate with the spectrometer, and injecting the anesthetic drug into the patient when no blood is detected in the aspirate. As mentioned previously, the presence of blood may be signaled if a threshold value is or is not met by the spectrometer, and the absence of blood may be signaled if a second threshold value is or is not met. The threshold value and the second threshold value may or may not be equal to each other, and may depend on one or more parameters. Alternatively, a user may modify a threshold value and/or a second threshold value in order to change the precision and/or accuracy of the blood detection. Furthermore, a signal to a user that no blood is detected may or may not depend on forming an aspirate in the drug cartridge. For instance, a syringe may signal that no blood is detected even before aspiration has occurred. Alternatively, a signal that blood is or is not present may occur during and after aspiration. Alternatively, the needle is pre-mounted onto the aspirator syringe, and/or the drug cartridge is pre-loaded into the aspirator syringe, and the method involves aspirating, detecting, and injecting. In the embodiment where the piston-engaging tip is a harpoon or similar shape, the harpoon may be inserted into the piston before aspirating. A user may aspirate the syringe by moving the plunger away from the needle mount. In some cases, a user may first need to eject a volume of the drug from the drug cartridge in order to have the available space to aspirate by moving the piston away from the needle. For a manual self-aspirating syringe, such as the syringe 10 of FIG. 2, aspiration may be performed by applying moderate pressure to the plunger 18 or to a bushing 46 in order to push a drug cartridge forward and deform the membrane of the drug cartridge. An annular stud 44 or other shape may project into the barrel interior in order to deform the membrane. Releasing the pressure on the cartridge restores the membrane shape and creates a negative pressure within the cartridge, which withdraws an aspirate through the needle. In some instances, a user may insert a needle into a tissue of a patient and aspirate at more than one needle depth prior to injecting a drug. Detecting aspirates from more than one needle depth at a specific injection point may help a user avoid injecting into a patient's blood vessel.

In one embodiment, where the computing device 106 is electrically connected to the spectrometer 24, the electric motor 90, the pressure sensor 108 in the plunger, and the sensor 110 in the piston-engaging tip, the electric motor may be able to automatically slide the plunger 18 to engage the piston-engaging tip 22 within the piston of a loaded drug cartridge. Having attached a needle to the needle mount, a user may stick the needle into a tissue of a patient and press a switch or other control on the syringe to begin an aspiration process. The motor may then move the plunger and the piston away from the first end to create an aspirate in the drug cartridge, and a light may signal if blood is or is not detected in the aspirate by the spectrometer. In one embodiment, the syringe may next automatically inject a volume from the drug cartridge if blood is not detected. In another embodiment, a syringe may aspirate automatically, and then prompt a user to choose to aspirate again or to inject a volume from the drug cartridge. Using feedback from the pressure sensor on the plunger and the plunger's position relative to the drug cartridge, the computing device may be able to control the electric motor to inject at a constant pressure or a constant flow rate. The motor may be able to stop once a certain volume has been injected or aspirated. In another embodiment, the motor may be able to inject at a slowly increasing pressure, in order to reduce pain to a patient. In another embodiment, where the computing device may control the motor according to stored instructions, a button or switch may exist for a user to override the computing device and directly control the motor. In another embodiment, the syringe may aspirate by pressing the drug cartridge towards the needle mount in order to deform the membrane. In an alternative embodiment, the aspirator syringe may be used to intentionally locate a patient's blood vessel to inject a drug or other substance into the blood vessel. In another embodiment, the aspirator syringe may be coupled or used with ultrasonography or other medical imaging techniques.

The invention claimed is:

1. An aspirator syringe comprising:
 a hollow syringe barrel with a needle mount extending outwards from a first end of the barrel;
 a plunger extending from a second end of the barrel and slidably moveable within the barrel, the plunger having a piston-engaging tip extending into the barrel;
 a spectrometer attached to a side of the barrel, the spectrometer configured to detect blood in an aspirate;
 wherein the spectrometer comprises a photodetector, the photodetector being in direct contact with an interior side of the barrel; and
 wherein the aspirator syringe further comprises a first indicator light on an exterior side of the barrel electrically connected to the spectrometer to indicate if blood has been detected during aspiration.

2. The aspirator syringe of claim 1 further comprising:
 a thumb rest attached to an end of the plunger distal to the piston-engaging tip; and
 a finger grip attached to and in direct contact with an exterior surface of the barrel adjacent to the second end.

3. The aspirator syringe of claim 1 wherein the piston-engaging tip is a harpoon having a pointed shape in the form of a cone, a pyramid, or an arrowhead, and
 wherein the pointed shape has a pointed tip at an end distal to the plunger.

4. The aspirator syringe of claim 1 further comprising a battery electrically connected to the spectrometer.

5. The aspirator syringe of claim 1 wherein the needle mount is removably attached to the first end of the barrel by a screw thread connection, and
 wherein the screw thread connection is between a screw thread on the needle mount and a complementary thread on an interior of the first end of the barrel.

6. The aspirator syringe of claim 1 further comprising a bushing located within the barrel and attached by a spring to the second end, wherein the bushing is traversed by the plunger and configured to secure a drug cartridge within the barrel.

7. The aspirator syringe of claim 1 wherein the spectrometer comprises an LED light source.

8. The aspirator syringe of claim 1 wherein the spectrometer is a spectrophotometer and detects an absorbance of a wavelength from 400 to 680 nm.

9. The aspirator syringe of claim 1 further comprising a second indicator light on the exterior side of the barrel and electrically connected to the spectrometer to indicate if blood has not been detected during aspiration.

10. A method of administering an anesthetic injection to a tissue of a patient with the aspirator syringe of claim 1, the method comprising:
 inserting an anesthetic syringe needle mounted onto the needle mount of the aspirator syringe into the tissue of the patient, wherein the aspirator syringe is loaded with a drug cartridge comprising an anesthetic drug;
 aspirating the aspirate into the drug cartridge;
 detecting the presence or absence of blood in the aspirate with the spectrometer; and injecting the anesthetic drug into the patient when no blood is detected in the aspirate.

* * * * *